July 17, 1956 H. M. TIRET Plant Pat. 1,498
FUCHSIA PLANT
Filed Sept. 21, 1955
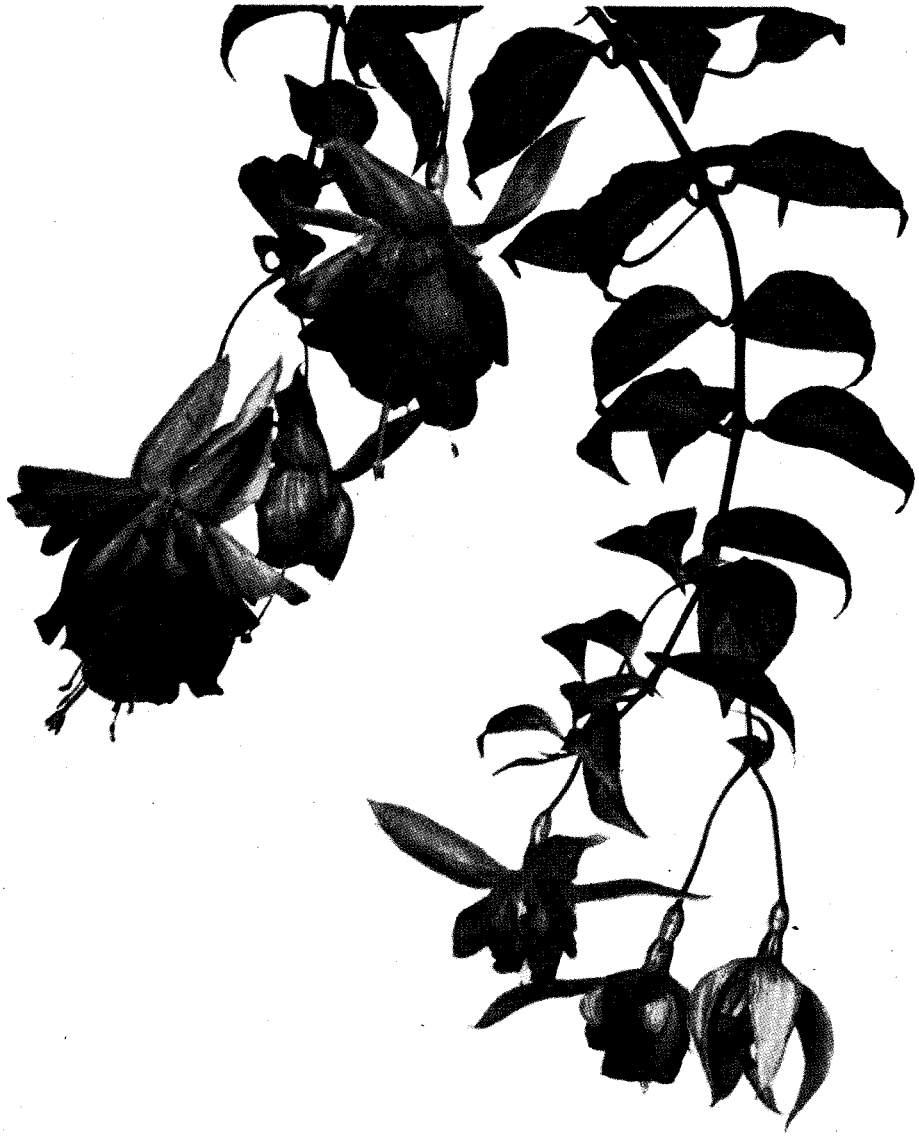

United States Patent Office

Plant Pat. 1,498
Patented July 17, 1956

1,498

FUCHSIA PLANT

Horace M. Tiret, San Francisco, Calif.

Application September 21, 1955, Serial No. 535,776

1 Claim. (Cl. 47—60)

This invention relates to a new and improved fuchsia plant, the principal new and different characteristic of which is the unique form combined with the exceptionally large flowers, together with the flaring of the center petals in a manner unlike any other fuchsia plant of such extreme size.

As a hybrid from a seedling (unpatented) not introduced to the trade, namely, 3–39–12 (female) and 6–14–3 (male) (unpatented), the figures representing applicant's own breeding symbols. The fuchsia plant is distinguished principally by the fact that this is a flower of extreme size, wherein the four center petals give it an appearance unlike any fuchsia of its type. The plant has been asexually reproduced at Palo Alto, California, by cuttings which retained the characteristics of the parent fuchsia.

The plant is a trailing variety and grows vigorously. It is a medium bloomer, and in extremely cool locations the blooms are scattered, but are of tremendous size. In warm growing areas, the plant is a more prolific bloomer. When the flower first opens, the main petals are aconite violet (British Horticultural Color Chart No. 937–1). At full maturity, the outer area of the main petals is aconite violet, tending toward dianthus purple (British Horticultural Color Chart No. 730) at the inner area toward the base. The outer petals of the flower, both immature and mature, are mottled at the base and colored Spinel Pink (British Horticultural Color Chart No. 0625). The tube and sepals are similarly colored, except that the top side of the sepals is Spinel Pink (British Horticultural Color Chart No. 0625–3) mottled with white. There is no appreciable fading in the sepals or the tube as the flower matures.

In the accompanying drawing, the figure shows a typical branch tip, the drawing representing approximate actual size.

A detailed description of this new variety of fuchsia plant follows:

*Habit of growth.*—Trailing variety with the branches trailing and arching downward, resulting in a good, willowy grower. The branches tend to be fairly loose in growth, with the flowers evenly spaced among the foliage. The plant is a medium bloomer, but more prolific in warmer growing areas.

*Foliage.*—The leaves are medium in size and dark green. The mature leaf is approximately 3 inches in length and 1¼" in width at the widest point, at maturity. The leaves are medium veined, with medium serrated edges. The foliage has a slight, crinkly effect.

*Flower.*—The petals number approximately twenty-six. The four center petals are very large and flare out in a unique fashion, as more particularly appears from the accompanying photograph. The corolla is exceptionally large and flaring. The diameter of the open, mature flower is approximately four inches. The length of the large center petals is approximately 2½", and the width is approximately 2¼", measured at maturity. The petals are smooth and crisp in appearance. When first open, the main petals are aconite violet (British Horticultural Color Chart No. 937–1). At maturity, the area of the main petals toward the base is dianthus purple (British Horticultural Chart No. 730). The outer petals of the flower, at all stages of development, are marbled at the base, and colored Spinel Pink (British Horticultural Color Chart 0625).

*Ovary.*—Green, with brown stripes, in color. The length is ⅝", and the width, at the widest point, is 5/16", measured at maturity.

*Tube.*—Medium long and narrow. The length is approximately 9/16" and the width, at the widest point, is approximately 5/16", measured at maturity.

*Sepals.*—The sepals are four in number, approximately 2½" in length, and ⅞" in width, measured at maturity. The sepals are medium broad, long, and recurved, when the flower is fully mature. The underside of the sepals has a crepe-like appearance, while the outer surface is smooth and satiny.

*Pistil.*—The style is approximately 3¾" from the tip of the ovary, and 1/32" in width, measured at maturity. The style is pale pink in color, and the stigma is white.

*Stem.*—The stem is reddish brown. It is approximately 2¾" in length, and 1/16" in width, measured at maturity.

*Stamens.*—The stamens are eight in number. The color is Spinel Pink, with maroon anthers. The stamens are very slender, and measure approximately 2½" in length at maturity.

*Parentage.*—Applicant's own seedlings (unpatented) not introduced to the trade, applicant's breeding symbol No. 3–39–12 (female) and 6–14–3 (introduced to the trade October, 1954) (millionaire) (male) (unpatented).

It is noted that the foliage and flowers will vary somewhat with the seasons and growing conditions; however, the fuchsia plant is clearly differentiated from others by its form and color, the outstanding characteristic of which is its unique form, combined with exceptionally large flowers.

Having thus disclosed my discovery, I claim:

A new and distinct variety of fuchsia plant herein described, and illustrated, characterized by the extremely large size of the four center petals which give it an appearance unlike any fuchsia of its type, with particular regard to the exceptionally large, flaring corolla.

No references cited.